(12) United States Patent
Murray et al.

(10) Patent No.: US 9,855,368 B2
(45) Date of Patent: *Jan. 2, 2018

(54) BONE MORPHOGENIC PROTEIN BINDING PEPTIDE

(71) Applicant: THE REGENTS OF THE UNIVERSITY OF CALIFORNIA, Oakland, CA (US)

(72) Inventors: Samuel S. Murray, Saugus, CA (US); Elsa J. Murray, Saugus, CA (US); Jeffrey C. Wang, Sherman Oaks, CA (US); Keyvan Behnam, Simi Valley, CA (US)

(73) Assignees: The Regents of the University of California, Oakland, CA (US); Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/640,451

(22) Filed: Mar. 6, 2015

(65) Prior Publication Data

US 2015/0246158 A1    Sep. 3, 2015

Related U.S. Application Data

(60) Division of application No. 13/486,498, filed on Jun. 1, 2012, now Pat. No. 8,975,231, which is a
(Continued)

(51) Int. Cl.
*A61L 27/22* (2006.01)
*C12N 5/0775* (2010.01)
(Continued)

(52) U.S. Cl.
CPC ............ *A61L 27/227* (2013.01); *A61K 35/28* (2013.01); *A61K 38/12* (2013.01);
(Continued)

(58) Field of Classification Search
None
See application file for complete search history.

(56) References Cited

U.S. PATENT DOCUMENTS 4,789,732 A    12/1988  Urist
4,843,063 A    6/1989   Seyedin et al.
(Continued)

FOREIGN PATENT DOCUMENTS

EP    0409472 A1    1/1991
JP    4235197 A     8/1992
(Continued)

OTHER PUBLICATIONS

U.S. Appl. No. 14/755,408, filed Jun. 30, 2015.*
(Continued)

*Primary Examiner* — David Romeo
(74) *Attorney, Agent, or Firm* — McDermott Will & Emery LLP

(57) ABSTRACT

A cyclized peptide designated BMP Binding Peptide (BBP) is a synthetic peptide that avidly binds rhBMP-2, as do endogenous forms of BBP, and sequence conservation between species results in a variety of useful BBP compositions. BBP increases the over-all osteogenic activity of rhBMP-2, increases the rate at which rhBMP-2 induces bone formation, and BBP induces calcification alone. Compositions and substrates including BBP, and methods of using BBP are useful in therapeutic, diagnostic and clinical applications requiring calcification and osteogenesis.

27 Claims, 9 Drawing Sheets

Related U.S. Application Data continuation of application No. 11/985,745, filed on Nov. 16, 2007, now Pat. No. 8,193,312, which is a continuation-in-part of application No. 10/587,313, filed as application No. PCT/US2005/002722 on Jan. 28, 2005, now Pat. No. 8,188,219.

(60) Provisional application No. 60/539,903, filed on Jan. 28, 2004.

(51) Int. Cl.
    *A61K 35/28* (2015.01)
    *A61K 38/12* (2006.01)
    *A61K 38/18* (2006.01)
    *C07K 14/51* (2006.01)
    *C07K 7/08* (2006.01)
    *A61L 27/38* (2006.01)
    *A61L 27/54* (2006.01)

(52) U.S. Cl.
    CPC ...... *A61K 38/1841* (2013.01); *A61K 38/1875* (2013.01); *A61L 27/3821* (2013.01); *A61L 27/3834* (2013.01); *A61L 27/54* (2013.01); *C07K 7/08* (2013.01); *C07K 14/51* (2013.01); *C12N 5/0668* (2013.01); *A61L 2400/18* (2013.01); *A61L 2430/02* (2013.01); *C12N 2501/15* (2013.01); *C12N 2501/155* (2013.01)

(56) References Cited

U.S. PATENT DOCUMENTS

| | | | |
|---|---|---|---|
| 5,158,934 | A | 10/1992 | Ammann et al. |
| 5,393,739 | A | 2/1995 | Bentz et al. |
| 5,407,810 | A | 4/1995 | Builder et al. |
| 5,620,867 | A | 4/1997 | Kiefer et al. |
| 5,981,483 | A | 11/1999 | Dennis et al. |
| 6,200,606 | B1 | 3/2001 | Peterson et al. |
| 6,311,690 | B1 | 6/2001 | Jefferies |
| 6,291,428 | B1 | 9/2001 | Macauley et al. |
| 6,322,786 | B1 | 11/2001 | Anderson |
| 7,241,874 | B2 | 7/2007 | Thorne |
| 8,188,219 | B2 | 5/2012 | Murray et al. |
| 8,193,312 | B2 | 6/2012 | Murray et al. |
| 8,415,302 | B2 | 4/2013 | Murray et al. |
| 8,759,296 | B2 | 6/2014 | Murray et al. |
| 8,975,231 | B2 * | 3/2015 | Murray .............. A61K 38/1841 424/426 |
| 9,050,300 | B2 * | 6/2015 | Murray .............. A61K 38/1841 |
| 9,072,709 | B2 * | 7/2015 | Murray .............. A61K 38/1841 |
| 9,610,320 | B2 * | 4/2017 | Murray .............. A61K 38/12 |
| 2003/0095993 | A1 | 5/2003 | Bentz et al. |
| 2006/0270645 | A1 | 11/2006 | Parhami |
| 2007/0056050 | A1 | 3/2007 | Clokie et al. |
| 2007/0065415 | A1 | 3/2007 | Kleinsek et al. |
| 2008/0234219 | A1 | 9/2008 | Brunkow et al. |
| 2008/0241108 | A1 | 10/2008 | Murray et al. |
| 2008/0268012 | A1 | 10/2008 | Behnam et al. |
| 2009/0047360 | A1 | 2/2009 | Murray et al. |
| 2013/0095139 | A1 * | 4/2013 | Murray .............. A61K 38/1841 424/400 |
| 2013/0303449 | A1 | 11/2013 | Murray et al. |

FOREIGN PATENT DOCUMENTS

| | | |
|---|---|---|
| JP | 5085939 A | 4/1993 |
| JP | H09505305 A | 5/1997 |
| WO | WO1996021006 A1 | 7/1996 |
| WO | WO1997031661 A1 | 9/1997 |
| WO | WO1997040137 A1 | 10/1997 |
| WO | WO2004004630 A2 | 1/2004 |
| WO | WO2004013294 A2 | 2/2004 |
| WO | WO2004097424 A1 | 11/2004 |
| WO | WO2005072403 A2 | 8/2005 |
| WO | WO2006093545 A1 | 9/2006 |
| WO | WO2008079400 A2 | 8/2008 |
| WO | WO2009067177 A2 | 5/2009 |

OTHER PUBLICATIONS

International Search Report and Written Opinion for PCT/US2005/002722 dated Dec. 19, 2005.
International Search Report and Written Opinion for PCT/US2005/043215 dated Aug. 3, 2006.
International Search Report and Written Opinion for PCT/US2007/026315 dated Jun. 17, 2008.
International Search Report and Written Opinion for PCT/US2008/012833 dated May 4, 2009.
Search Report for European Patent Application No. 05857032 dated Jul. 21, 2009.
Search Report for European Patent Application No. 07868028 dated Jul. 6, 2011.
Search Report for European Patent Application No. 08852773 dated Jul. 6, 2011.
Search Report for European Patent Application No. 10797441 dated Jun. 21, 2013.
Behnam, et al. "Alkali-urea Extraction of Demineralized Bone Matrix Removes Noggin, an Inhibitor of Bone Morphogenetic Proteins." Connective Tissue Research 2004, vol. 45, No. 4-5, pp. 257-260 (Jul. 2004).
Behnam, et al. "BMP Binding Peptide: a BMP-2 Enhancing Factor Deduced from the Sequence of Native Bovine Bone Morphogenetic Protein/Non-Collagenous Protein." Journal of Orthopaedic Research, vol. 23, pp. 175-180 (2005).
Behnam, et al. "Identification of the Molecular Chaperon Alpha B-Crystallin in Demineralized Bone Powder and Osteoblast-Like Cells." Journal of Orthopaedic Research, vol. 20(6), pp. 1190-1196 (Nov. 2002).
Bender, et al. "Sickle Cell Disease." NCBI Bookshelf. A service of the National Library of Medicine, National Institutes of Health, 1993-2013, Bookshelf ID: NBK1377PMID: 20301551.
Bennett, et al. "Characterization of the Human Secreted Phosphoprotein 24 Gene (SPP2) and Comparison of the Protein Sequence in Nine Species." Matrix Biology, vol. 22, No. 8, pp. 641-651 (2004).
Bowie, et al. "Deciphering the Message in Protein Sequences: Tolerance to Amino Acid Substitutions." Science, vol. 247, Mar. 16, 1990, pp. 1306-1310.
Brown, et al. "Friends and Relations of the Cystatin Superfamily-New Members and Their Evolution." Protein Science, vol. 6, pp. 5-12 (1997).
Carano, et al. "Angiogenesis and Bone Repair." Drug Discovery Today, vol. 8(21), pp. 980-989 (Nov. 2003).
Chen, et al. "Bone Morphogenetic Proteins" Growth Factors, vol. 22, No. 4, pp. 233-241 (Dec. 2004).
Cook, et al. "In Vivo Evaluation of Recombinant Human Osteogenic Protein (rhOP-1) Implants as a Bone Graft Substitute for Spinal Fusions." Spine, vol. 19, No. 15, pp. 1655-1663 (1994).
Cook et al. "Recombinant Human Bone Morphogenetic Protein-7 Induces Healing in a Canine Long-Bone Segmental Defect Model." Clinical Orthopaedics and Related Research, No. 301, pp. 302-312 (1994).
Demetriou, et al. "Fetuin/α2-HS Glycoprotein is a Transforming Growth Factor-β Type II Receptor Mimic and Cytokin Antagonist." Journal of Biological Chemistry, vol. 271(22), pp. 12755-12761 (May 1996).
Dijke, et al. "Controlling Cell Fate by Bone Morphogenetic Protein Receptors." Molecular and Cellular Endocrinology, vol. 211, pp. 105-113 (2003).
Guo, et al. "Protein Tolerance to Random Amino Acid Change." Proc. Natl. Acad. Sci. U.S.A. Jun. 22, 2004; 101(25):9205-10.
Herrera-Esparza, et al. "An Activin Receptor IA/Activin-Like Kinase-2 (R206H) Mutation in Fibrodysplasia Ossificans Progressiva." Hindawi Publishing Corporation Case Reports in Genetics, vol. 2013, Article ID 260371 (2013).

(56) References Cited

OTHER PUBLICATIONS

Hu, et al. "Isolation and Molecular Cloning of a Novel Bone Phosphoprotein Related in Sequence to the Cystatin Family of Thiol Protease Inhibitors." Journal of Biological Chemistry, vol. 270(1), pp. 431-436 (Jan. 1995).

Madian, et al. "Effect of Single Amino Acid Substitution on Oxidative Modifications of the Parkinson's Disease-Related Protein, DJ-1." Molecular & Cellular Proteomics 11.2 (2012).

Mamidi, et al. "Alanine or aspartic acid substitutions at serine23/24 of cardiac troponin I decrease thin filament activation, with no effect on crossbridge detachment kinetics." Arch Biochem Biophys., vol. 525 (2012).

Miller-Bertoglio, et al. "Maternal and Zygotic Activity of the Zebrafish ogon Locus Antagonizes BMP Signaling." Developmental Biology, vol. 21, pp. 72-89 (1999).

Murray, et al. "Strain-Dependent Differences in Vertebral Bone Mass, Serum Osteocalcin, and Calcitonin in Calcium-Replete and -Deficient Mice." Pro. Soc. Exp. Biol. Med., vol. 203, pp. 64-73 (1993).

Murray, et al. "Recombinant Expression, Isolation, and Proteolysis of Extracellular Matrix-Secreted Phosphoprotein-24 kDa." Connect Tissue Res. 2007; 48(6):292-9.

Ngo, et al. "Computational Complexity, Protein Structure Prediction, and the Levinthal Paradox." The Protein Folding Problem and Tertiary Structure Prediction, Aug. 1994, Springer Verlag, pp. 433 and 492-495.

Notredame, et al., "T-Coffee: A Novel Method for Fast and Accurate Multiple Sequence Alignment." Journal of Molecular Biology, vol. 302, pp. 205-217 (2000).

Parfitt, et al. "Bone Histomorphometry: Standardization of Nomenclature, Symbols, and Units." Journal of Bone and Mineral Research, vol. 2(6) pp. 595-610 (1987).

Perron, et al. "Structural distinctions in BMPs underlie divergent signaling in spinal neurons." Neural Development, 7:16 (2012).

Ripamonti, et al. "Xenogeneic Osteogenin A Bone Morphogenetic Protein and Demineralized Bone Matrices Including Human Induce Bone Differentiation in Athymic Rats and Baboons." Matrix: Collagen and Related Research, vol. 11, No. 6, pp. 404-411 (Jan. 1991).

Sampath, et al. "Dissociative Extraction and Reconstitution of Extracellular Matrix Components involved in Local Bone Differentiation." Proceedings of the National Academy of Sciences of USA, vol. 78, No. 12, pp. 7599-7603 (Dec. 1981).

Sintuu, et al. Full-Length Bovine spp24 [spp24 (24-203)] Inhibits BMP-2 Induced Bone Formation. Journal of Orthopaedic Research, Jun. 2008, pp. 753-758.

Sintuu, et al. "Full-Length spp24, but Not Its 18.5-kDa Proteolytic Fragment, Inhibits Bone-Healing in a Rodent Model of Spine Fusion." Journal of Bone and Joint Surgery, vol. 93-A, No. 11, pp. 1022-1032 (2011).

Takahashi. "Bone Morphogenetic Protein (BMP): From Basic Studies to Clinical Approaches." Folia Pharmacologica Japonica, vol. 116, No. 4, pp. 232-240 (Oct. 2000).

Urist, et al. "Hydroxyapatite Affinity, Electroelution, and Radioimmunoassay for Identification of Human and Bovine Bone Morphogenetic Proteins and Polypeptides." Development and Diseases of Cartilage and Bone Matrix, pp. 149-176 (1987).

Urist, et al. "Preparation and Bioassay of Bone Morphogenic Protein and Polypeptide Fragments." Methods in Enzymology, vol. 146, pp. 294-312 (1987).

Urist, et al. "Purification of Bovine Bone Morphogenetic Protein by Hydroxyapatite Chromatography." Proc. Natl. Acad. Sci. USA, vol. 81, pp. 371-375 (Jan. 1984).

Urist. "Bone: Formation by Autoinduction." Science, vol. 150, pp. 893-899 (Nov. 1965).

Urist. "Emerging Concepts of Bone Morphogenetic Protein." Fundamentals of Bone Growth: Methodology and Applications, pp. 189-198 (1991).

Zhao, et al. "Targeted Overexpression of Insulin-Like Growth Factor I to Osteoblasts of Transgenic Mice: Increased Trabecular Bone Volume Without Increased Osteoblast Proliferation." Endocrinology, vol. 141(7), pp. 2674-2682 (2000).

Supplementary European Search Report for EP05857032 dated Aug. 7, 2009.

\* cited by examiner

SEQ ID No 1:   Cys-Arg-Ser-Thr-Val-Arg-Met-Ser-Ala-Glu-Gln-Val-Gln-Asn-Val-Trp-Val-Arg-Cys
SEQ ID No 2:   TGC-AGA-AGC-ACC-GTG-CGG-ATG-TCT-GCT-GAA-CAG-GTG-CAG-AAC-GTG-TGG-GTT-CGC-TGC

FIG. 1A leader sequence    BMP-2 homology region    cystatin homology region (1) MAMKNLVIFVLSMNHWTCTGFPVYQYDPASLKEALSASVAKVNSQSLSPYLRAAPRSSVKRVNALDEDSLTMDLE (75)

cystatin homology region    TGF-β receptor II homology region

(76) FRIQETTCCRESEADPATCDPQRGYHPVAVCRSTVRNSAEQVQNVWVRCHWSSSSSSSSEEMFFGDILGSSTS (150)

(151) RHSVLLGLTPDRSRGEPLYEPSREMKKNPLGNRRYSMPWPRARVNPGPE (200) S

| human BMP-2 | F | P | L | A | D | H | L | N | S | T | N | H | A | I | V | Q | T | L | V | N | S | V | N | S | K | SEQ ID NO 6 |
|---|---|---|---|---|---|---|---|---|---|---|---|---|---|---|---|---|---|---|---|---|---|---|---|---|---|---|
| human BMP-2 | F | P | V | Y | D | P | A | S | L | K | E | A | L | S | A | S | V | A | K | V | S | N | S | Q | | SEQ ID NO 7 |
| | | | C | | | | | | | C | | | | C | | C | | C | | | C | | C | | | |

FIG. 2

| bovine fetuin | 114 | C | D | I | H | V | L | K | Q | D | G | Q | F | S | V | L | F | T | K | C | | SEQ ID NO 8 |
|---|---|---|---|---|---|---|---|---|---|---|---|---|---|---|---|---|---|---|---|---|---|---|
| human TGF-β receptor II | 84 | C | * | V | A | V | W | K | N | D | E | N | L | L | F | T | V | C | | | | SEQ ID NO 9 |
| | | | | | | | | | | | | | | | | | | | | | | |
| human TGF-β receptor II | 84 | C | V | W | R | K | M | S | A | E | Q | N | I | T | L | L | E | T | V | C | | SEQ ID NO 9 |
| bovine BBP | | - | - | C | - | - | - | C | - | - | - | - | C | - | C | Y | R | E | T | * | C | SEQ ID NO 10 |

FIG. 3

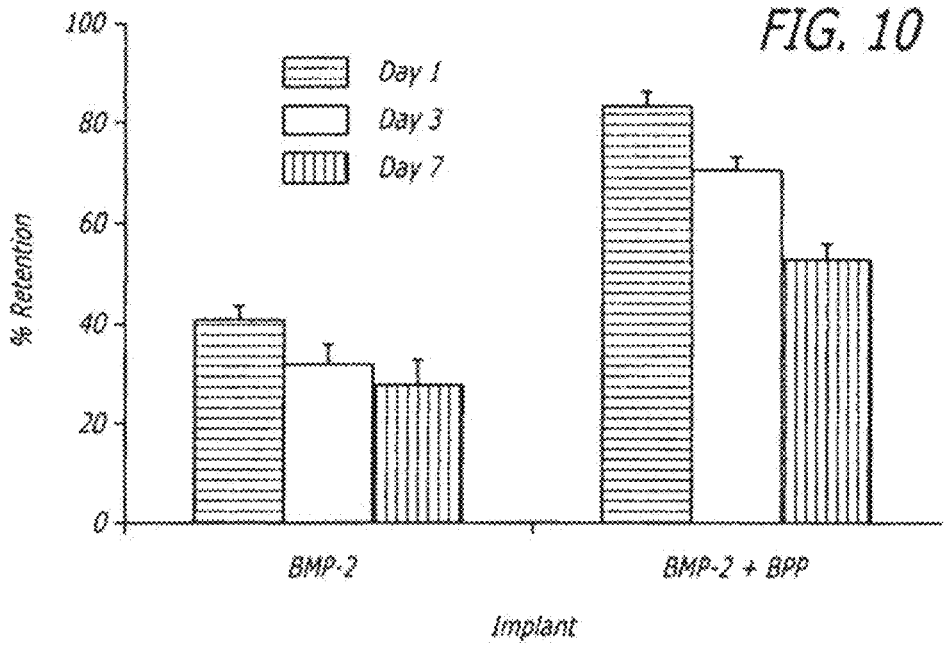
FIG. 10
FIG. 11
IQETTCRRESEADPATCDFQRGYHVPVAVCRSTVRMSAEQV (SEQ ID No 3)
CGEPLYEPSREMRRN* (SEQ ID No 4) (SEQ ID No 4)
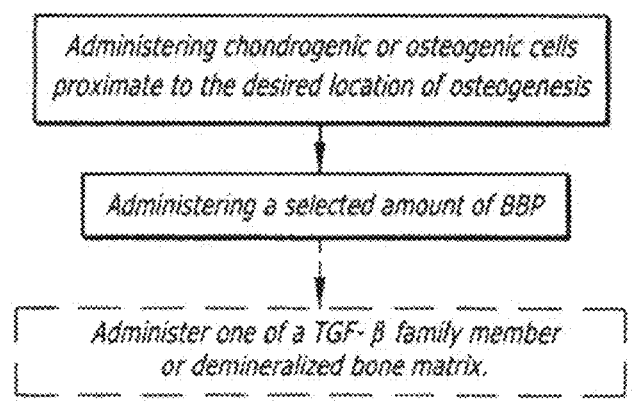
FIG. 12A

FIG. 14A

| Species | Position/Amino acid | 1 | 2 | 3 | 4 | 5 | 6 | 7 | 8 | 9 | 10 | 11 | 12 | 13 | 14 | 15 | 16 | 17 | 18 | 19 | SEQ ID No. |
|---|---|---|---|---|---|---|---|---|---|---|---|---|---|---|---|---|---|---|---|---|---|
| Consensus | | C | R | S | T | V | X | X | S | X | X | X | V | X | X | V | X | X | X | C | 11 |
| Bovine | | C | R | S | T | V | R | M | S | A | E | Q | V | Q | N | V | W | V | R | C | 1 |
| Human | | C | R | S | T | V | K | V | S | A/V* | Q | Q | V | Q | G | V | H | A | R | C | 13 |
| Porcine | | C | R | S | T | V | Q | L | S | A | E | K | V | Q | D | V | W | V | R | C | 15 |
| Ovine | | C | R | S | T | V | R | M | S | A | E | R | V | Q | D | V | W | V | R | C | 17 |
| Rat | | C | R | S | T | V | Q | M | S | K | G | Q | V | K | D | V | W | A | H | C | 19 |
| Mouse | | C | R | S | T | V | Q | M | S | K | G | Q | V | K | D | V | W | A | H | C | 21 |
| Chicken | | C | K | S | V | V | E | V | S | S | E | Q | L | V | N | V | I | V | R | C | 23 |
| Salmon | | C | T | A | R | V | R | V | T | A | E | F | T | Q | V | V | S | L | N | C | 25 |
| Trout | | C | T | A | R | V | R | V | T | A | E | L | T | Q | V | V | S | L | N | C | 27 |

* The amino acid at position 9 can be either A or V.

FIG. 14B

SEQ ID No. 12: TGC AGA AGC ACC GTG XXX YYY TCT XXX XXX XXX GTG XXX XXX GTG XXX TTT TTT TGC

SEQ ID No. 14: TGC AGA AGC ACC GTG AAG GTA TCT GCC CAG CAG GTG CAG GGC GTG CAT GCT CGC TGC

SEQ ID No. 16: TGC AGA AGC ACC GTG CAG ATA TCT GCT GAG AAG GTG CAG GAT GTG TCG GTG CGT TGT

SEQ ID No. 18: TGC AGA AGC ACC GTG CGG ATG TCT GCT GAA CCC GTG CAG CAC GTG TGG GTT CGC TGC

SEQ ID No. 20: TGC AGG AGC ACA GTG CAG ATG TCC AAG GGA CAG GTG AAG GAT GTG TGG GCT CAC TGC

SEQ ID No. 22: TGC AGG AGC ACT GTG CAG ATG TCC AAG GGA CAG GTA AAG GAT GTG TGG GCT CAC TGC

SEQ ID No. 24: TGC AAA AGC GTT GTA GAA GTC TCC AGT GAG CAG ATT GTG AAT GTT ATT GTG CGA TGC

SEQ ID No. 26: TGC ACC GCA CGT GTT CGC GTC ACT GTC ACT GCA GAG TTC ACT CAG GTT GTG TCC CTG AAC TGT

SEQ ID No. 28: TGC ACC GCA CGT GTT CGT GTC ACT GCA GAG CTC ACT GCA GAG GTT GTG TCC CTG AAC TGT

BONE MORPHOGENIC PROTEIN BINDING PEPTIDE

PRIORITY CLAIM

This application is a divisional of U.S. patent application Ser. No. 13/486,498, which was filed on Jun. 1, 2012, now U.S. Pat. No. 8,975,231, issued on Mar. 10, 2015, which is a continuation of U.S. patent application Ser. No. 11/985,745, filed Nov. 16, 2007, now U.S. Pat. No. 8,193,312, issued Jun. 5, 2012, which is a continuation-in-part of U.S. application Ser. No. 10/587,313, filed on Apr. 28, 2008, now U.S. Pat. No. 8,188,219, issued May 29, 2012, which claims priority from U.S. Provisional Patent Application 60/539,903 filed Jan. 28, 2004.

GOVERNMENT SUPPORT

This invention was made with Government support under AR053259 awarded by the National Institutes of Health. The Government has certain rights in the invention. This work was supported by the U.S. Department of Veterans Affairs, and the Federal Government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 20, 2010, is named 38586357.txt and is 11,264 bytes in size.

BACKGROUND OF THE INVENTION

Growth factors are substances, including peptides, which affect the growth and differentiation of defined cell populations in vivo or in vitro. Normal bone formation occurs during development, bone remodeling occurs in adult life, and bone repair occurs in order to preserve the integrity of the skeleton. Bone formation, remodeling and repair involve bone resorption by osteoclasts and bone formation by osteoblasts. Cell differentiation and the activity of osteoblasts and osteoclasts are regulated by growth factors. Thus, any interference between the balance in cell differentiation and resorption can affect bone homeostasis, bone formation and repair.

Osteoblasts are derived from a pool of marrow stromal cells (also known as mesenchymal stem cells). MSC are present in a variety of tissues and are prevalent in bone marrow stroma. MSC are pluripotent and can differentiate into chondrogenic or osteogenic cells including osteoblasts, chondrocytes, fibroblasts, myocytes, and adipocytes.

The induction of ectopic bone formation by demineralized bone matrix (DBM) has been described. (Urist, M. R.: Bone: Formation by autoinduction. *Science* 150:893-899, 1965; Urist, et al., Purification of bovine morphogenetic protein by hydroxyapatite chromatography. *Proc. Natl. Acad. Sci. USA* 81:371-375, 1984; Urist, M. R. Emerging concepts of bone morphogenetic protein. In *Fundamentals of Bone Growth: Methodology and Applications*, Boston C.R.C. Press, pp. 189-198, 1991.) Further, the properties of the partially purified protein fraction, bone morphogenic protein/non-collagenous protein ("BMP/NCP" or "BMP"s) have been described. (Urist, et al. Methods of Preparation and Bioassay of Bone Morphogenetic Protein and Polypeptide Fragments. In *Methods in Enzymology*. Vol. 146. New York, Academic Press, pp. 294-312, 1987; Urist, et al., Hydroxyapatite affinity, electroelution, and radioimmunoassay for identification of human and bovine bone morphogenetic proteins and polypeptides. In *Development and Diseases of Cartilage and Bone Matrix*. New York, Alan R, Liss, Inc., pp. 149-176, 1987.)

BMP/NCP was never purified to homogeneity, but other investigators have used similar starting materials to clone a number of recombinant "BMPs." However several of these molecules have little or no osteogenic activity. "BMPs" and other osteogenic factors have been studied for use in clinical applications. However, the cost of using minimally effective dosages of BMP-7, for example has been a limiting factor in clinical use. Therefore, effective and affordable compositions and methods are desired for clinical applications relating to bone.

BRIEF SUMMARY OF INVENTION

The inventions are related to a synthetic peptide designated BMP Binding Peptide (BBP) that avidly binds rhBMP-2. BBP increases the rate and degree to which rhBMP-2 induces bone formation. BBP alone induces calcification of chondrogenic, osteogenic and osteoblastic cells. Compositions and substrates including BBP, antibodies to BBP and methods of using BBP are useful in applications relating to bone.

The invention may include a method of systemic delivery or localized treatment with agents for maintaining bone homeostasis, enhancing bone formation and/or enhancing bone repair.

In one application of the invention, the method may be applied to induce the local repair of bone or to treat bone related disorders, such as osteoporosis.

The invention may also include implants having agents or seeded with pluripotential or differentiated cells for inducing bone formation or repair. The invention may also include the application of substances or differentiated cells at a site where bone formation or bone repair is desired.

This invention is advantageous at least in that BBP enhances calcification of chondrogenic or osteogenic precursor cells. Further, this invention is advantageous at least in that BBP enhances osteogenesis to occur faster to a greater extent, which may improve the clinical rate and effectiveness of treatment with BMP, and reduce doses and therefore the cost of treatment.

These, as well as other objects, features and benefits will now become clear from a review of the following detailed description of illustrative embodiments and the accompanying drawings.

BRIEF DESCRIPTION OF DRAWINGS

FIG. 1A are BBP bovine (1) amino acid and (2) nucleic acid sequences, respectively; FIG. 1B is a partial amino acid sequence of the bovine BMP binding protein ("BBP") showing the cystatin homology region, the BMP-2 homology region, and the TGF-β receptor II homology domain.

FIG. 2 is an amino acid sequence alignment of human BMP-2 and the BMP-2 homology region in bovine SPP-24; (i, identical; c, conservative substitution; sc, semi-conservative substitution).

FIG. 3 is an amino acid sequence alignment of bovine fetuin and human TGF-β receptor II (above) and of human TGF-β receptor II and the TGF-β receptor II homology domain of bovine SPP-24 (corresponding to BBP) (bottom); (i, identical; c, conservative substitution; sc, semi-conservative substitution).

FIG. 10 is a bar graph depicting the percentage of rhBMP-2 retention over 1, 3 and 7 days in the presence or absence of BBP.

FIG. 11 includes amino acid sequences against which specific SSP-24/BBP antibodies have been generated.

FIG. 14 A is a chart showing the amino acid sequences for BPP in various species. FIG. 14 B is a list of the nucleic acid sequences for BPP in various species.

DETAILED DESCRIPTION OF ILLUSTRATIVE EMBODIMENTS

Figure 4:
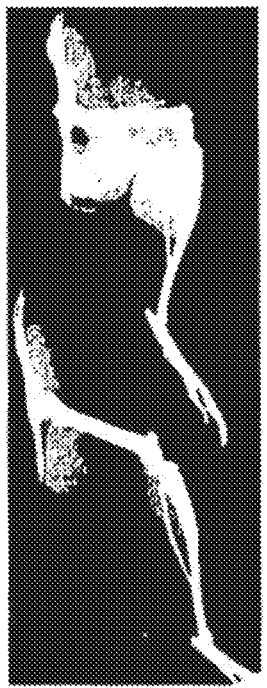
FIG. 4 is a radiogram of mouse hind quarters 21 days after implantation of 500 µg of BBP in atelocollagen (top) or atelocollagen alone (bottom).

One embodiment of the invention comprises a peptide having the amino acid sequence of SEQ ID NO: 1. The bovine derived amino acid SEQ ID NO: 1 has been designated BBP, and SEQ ID NO: 2 corresponds to the bovine nucleic acid sequence encoding BBP.

One embodiment of the invention comprises a peptide having the amino acid sequence of SEQ ID NO: 13, which is the sequence of human BBP. SEQ ID NO: 14 corresponds to the human nucleic acid sequence encoding human BBP.

BBP is a 19 amino acid, 2.1 kD peptide, derived from a 18.5 kD fragment of a known 24 kDa secreted phosphoprotein ("SPP-24"). SPP-24 is illustrated in FIG. 2. Notably, SPP-24 inhibits BMP-2 induced bone formation. BBP contains the cystatin-like domain of SPP-24. BBP is expressed at least in the liver and bone (including at least demineralized cortical bone and periosteum).

The BBP amino acid sequence is similar to the TGF-β/BMP-binding region of fetuin, a member of the cystatin family of protease inhibitors. BBP avidly binds rhBMP-2 (recombinant human BMP-2) with a $K_D$ of $\times10^{-5}$ M. BBP may also bind other molecules having similar binding domains to BMP-2, such as other TGF-β proteins (including but not limited to BMP-4 and BMP-7) and affect their retention rates and/or activity as well.

BBP alone induces calcification of vertebrate chondrogenic and osteogenic precursor cells. BBP increases the rate and degree to which rhBMP-2 induces bone formation. Surprisingly, BBP as used with BMP-2 in vivo causes osteogenesis to occur faster and to a greater extent and with smaller amounts of rhBMP-2.

For example, when implanted alone in mouse muscle, the BBP induces dystrophic calcification. The process of bone formation in repair or ectopic bone formation the "mouse hindquarter" or "muscle pouch" model recapitulates endochondral bone formation. The first step involves the production of cartilage, which is replaced by bone. This same process that occurs during endochondral bone formation in development, while some membraneous bone formation occurs directly without a cartilage intermediary.

In one embodiment of the invention, a peptide comprising a fragment of BBP may be useful, if the fragment similarly increases degree or rate of osteogenesis by BMP-2 in mammalian cells, or increases degree or rate of calcification in vertebrate cells, or specifically mammalian chondrogenic or osteogenic progenitor cells.

Forms of BBP having modifications of the amino acid SEQ. ID NO: 1 may also be useful in this invention. For example, the conserved amino acid sequences of BBP between species, deletional or insertional modifications, conservative or semi-conservative substitutional modifications are intended to be encompassed in the claimed BBP, to the extent that the modified amino acid sequences increase the residency time and or activity of BMP-2 or other TGF-β homologous molecules. BBP is a β-pleated sheet-turn-beat pleated sheet molecular motif ("B-T-B"). It is currently believed that growth factor binding amino acids reside in the T-section. Therefore, amino acid substitutions in the T-section may affect activity of BBP to a greater extent than substitutions in the B regions.

One embodiment of the invention comprises a peptide having the sequence of SEQ ID NO: 11: C-R-S-T-V-X-Z-S-X-X-X-V-X-X-V X-Z-Z-C, which is the mammalian consensus sequence for BBP. FIG. 14A shows the homology in amino acid sequence across bovine (SEQ ID NO: 1; nucleic acid sequence set forth at SEQ ID NO: 2), human (SEQ ID NO: 13; nucleic acid sequence set forth at SEQ ID NO: 14 (position 9 is either A or V), porcine (SEQ ID NO: 15; nucleic acid sequence set forth at SEQ ID NO: 16), ovine (SEQ ID NO: 17; nucleic acid sequence set forth at SEQ ID NO: 18), rat (SEQ ID NO: 19; nucleic acid sequence set forth at SEQ ID NO: 20), and mouse (SEQ ID NO: 21; nucleic acid sequence set forth at SEQ ID NO: 22) BBP. FIG. 14A also shows highly conserved regions in chicken (SEQ ID NO: 23; nucleic acid sequence set forth at SEQ ID NO: 24), salmon (SEQ ID NO: 25; nucleic acid sequence set forth at SEQ ID NO: 26) and trout (SEQ ID NO: 27; nucleic acid sequence set forth at SEQ ID NO: 28).

In FIG. 14 A, "X" and "Z" are used to denote amino acid substitutions that are understood to be semi-conservative or conservative, respectively. Conservative substitutions include amino acids selected from the same group, and semi-conservative substitutions include substitutions that are not believed to affect the BMP-2 binding domain or the function of the BBP. For example, the substitution at position 6 is conservative between human, rat and ovine, but semi-conservative with some other species because the amino acids reported at that position in different species are: Q and E (Q in porcine, rat, and mouse BBP, and E in chicken). Although K and R are both classified as basic amino acids, Q is classified as an uncharged polar amino acid, therefore the substitution is not conservative. The substitution is semi-conservative, however, because the function of BBP is believed to be unaffected. Semi-conservative substitutions are also found at positions 9, 10, 11, and 16. At position 9, the amino acids A is found in bovine, human, porcine and ovine BBP, compared to K in rat and mouse BBP. At position 10, the amino acid E is reported for bovine, porcine, and ovine BBP, human BBP contains Q at that position, and rat and mouse BBP contain the amino acid G. At position 11, the amino acid Q is found in bovine, human, rat and mouse, whereas K, is reported for porcine BBP and R for ovine BBP. At position 16, W is found in bovine, porcine, ovine, rat and mouse BBP, whereas human BBP contains an H. There are also semi-conservative substitutions at positions 13 and 14 between rat/human, as opposed to other species.

An example of a conservative substation is found at position 7. At this position, different hydrophobic amino acids are observed in different species, namely, M in bovine, ovine, rat, and mouse BBP, compared to V in human and I in porcine BBP. This substitution is considered conservative because M, V, and I are all hydrophobic amino acids. Other conservative substitutions occur at positions 17 and 18. Two hydrophobic amino acids, A and V, are found at position 17. At position 18, two basic amino acids, R and H, are found.

One embodiment of the invention may be a composition including BBP which increases degree or rate of calcification in vertebrate cells, or more specifically mammalian chondrogenic or osteogenic precursor cells. Further, the invention may be including BBP which increases degree or rate of osteogenesis by BMP-2, and one of BMP-2 or demineralized bone matrix. Further, the composition may additionally or alternatively include other TGF-β family members, including but not limited to BMP-4 or BMP-7. It is further noted that other TGF-β family members are involved in immune system function, and BBP may bind with an effect the residence time or activity of those molecules, as well which may effect immune function, inflammation or tumor growth.

In one embodiment, the invention may include a medicament for use in inducing the rate or degree of osteogenesis in a vertebrate including a therapeutically effective dosage of BBP and BMP or DBM. The invention may further include, a medicament for use in inducing the rate or degree of calcification in a vertebrate including a peptide comprising BBP.

Applications for BBP.

A number of applications for BBP are suggested from its pharmacological (biological activity) properties. For example, BBP alone or in combination with other TGF-family members such as BMP-2, BMP-4 and BMP-7, or demineralized bone matrix may be used in clinical or research methods for inducing bone formation, maintaining bone homeostasis and/or enhancing bone repair. BBP may be used alone or in combination to treat developmental or homeostatic bone disorders (such as osteoporosis), bone injury (such as fracture healing flat (e.g., membranous) and long (e.g., endochondral) bones [comment that this is equally applicable], non-union fractures and reconstructive surgery. The invention may also be used in treating periodontitis, periodontal regeneration, alveolar ridge augmentation for tooth implant reconstruction, treatment of non-union fractures, sites of knee/hip/joint repair or replacement surgery.

Clinical indices of a method or compounds ability to maintain bone homeostasis is evidenced by improvements in bone density at different sites through out the body as assessed, at least by DEXA scanning. Enhanced bone formation in a healing fracture is routinely assessed by regular X-ray of the fracture site at selected time intervals. More advanced techniques for determining the above indices, such as quantitative CT scanning or quantitative histological methods (eg., tissue is processed, stained, and microscopically examined and bone defined an measured with image analysis) may be used. Further, measures of bone density, bone area, bone mineral content, formation of ectopic bone, and increases in the opacity of tissue upon X-ray examination, expression of alkaline phosphatase activity, calcium incorporation, mineralization or expression of osteocalcin mRNA may be used to observe the effects of BBP calcification and/or osteogenesis.

The invention may also include the use of agents which inhibit osteoclastic bone resorption. Agents which may be useful in this invention to effect osteoclastic bone resorption include, but are not limited to, bisphosphonates, the selective estrogen receptor modulators, calcitonin, and vitamin D/calcium supplementation. The invention may also include the use of agents which induce osteoblastic bone formation. Agents which may be useful in this invention include, but are not limited to PTH, sodium fluoride and growth factors, such as insulin-like growth factors I and II.

The in vivo models used to show the calcification effects of BBP alone or osteogenic effects in combination with BMP have been used previously in demonstrating similar behaviors of other compounds. In particular, in vivo models have also previously been able to successfully predict the in vivo osteogenic effects of compounds such as BMP and insulin like growth factors (IGF). Specifically, it has been demonstrated that the osteogenic effects of BBP in an animal model using rat femur, ectopic bone formation model. Therefore it is anticipated that, based on these similar findings, BBP will have osteogenic effects in vivo in humans. Demonstration of osteogenic effects of a compound in these in vivo models are necessary prior to trials that would demonstrate their effects in vivo humans.

Therapeutically Effective Dose.

A therapeutically effective dose of BBP or a TGF-β family member useful in this invention is one which has a positive clinical effect on a patient or desired effect in cells as measured by the ability of the agent to enhance calcification or osteogenesis, as described above. The therapeutically effective dose of each agent can be modulated to achieve the desired clinical effect, while minimizing negative side effects. The dosage of the agent may be selected for an individual patient depending upon the route of administration, severity of the disease, age and weight of the patient, other medications the patient is taking and other factors normally considered by an attending physician, when determining an individual regimen and dose level appropriate for a particular patient.

This invention is advantageous in at least the dosage of BMP-2 required to induce a given rate or degree of osteogenesis may be reduced when BMP-2 is combined with BBP.

Dosage Form.

The therapeutically effective dose of an agent included in the dosage form may be selected by considering the type of agent selected and the route of administration. The dosage form may include a agent in combination with other inert ingredients, including adjutants and pharmaceutically acceptable carriers for the facilitation of dosage to the patient, as is known to those skilled in the pharmaceutical arts.

Therapeutic formulations of BBP (when claimed is intended to include modifications or fragments thereof), may be prepared for storage by mixing the BBP having the desired degree of purity with optional physiologically acceptable carriers, excipients or stabilizers, in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin or immunoglobulins. Other components can include glycine, blutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or poly(ethylene glycol) (PEG).

The dosage form may be provided in preparations for subcutaneous (such as in a slow-release capsule), intravenous, intraparitoneal, intramuscular, peri- or intraskeletal for example. Any one or a combination of agents may be included in a dosage form. Alternatively, a combination of agents may be administered to a patient in separate dosage forms. A combination of agents may be administered concurrent in time such that the patient is exposed to at least two agents for treatment.

Additional Agents.

The invention may include treatment with an additional agent which acts independently or synergistically with BBP to enhance calcification osteogenesis. For example, BBP may be combined with BMP, bisphosphonates, hormone therapy treatments, such as estrogen receptor modulators, calcitonin, and vitamin D/calcium supplementation, PTH (such as Forteo or teriparatide, Eli Lilly, sodium fluoride and growth factors that have a positive effect on bone, such as insulin-like growth factors I and II and TGF-β. Those skilled in the art would be able to determine the accepted dosages for each of the therapies using standard therapeutic dosage parameters, or reduced dosages where the effects of BBP are synergistic with the secondary agent, such as BMPs.

BBP is currently thought to act upon BMP-2 at least by increasing its residency time with a substrate. One embodiment of the invention is a method of detecting the ability of BBP to enhance the residency time of a TGF-β homologous molecule including applying an amount of the TGF-β homologous molecule at a first and second selected location. Further, applying a selected amount of BBP at the first selected location, and finally detecting the amount of the TGF-β homologous molecule at the first and second location after a selected time period; and calculating the difference between the amount of the TGF-β homologous molecule at the first and second location.

In one embodiment, the invention may include a method of enhancing the rate or degree of osteogenesis in vertebrate tissue including application of BBP which increases degree or rate of osteogenesis by BMP-2 in mammalian cells and one of a TGF-β family member, such as BMP-2 or demineralized bone matrix.

In one embodiment, the invention may include a method of inducing calcification of vertebrate tissue, or more specifically vertebrate chondrogenic or osteogenic precursor cells, including application of BBP.

In one embodiment, the invention may include a method of enhancing the rate or degree of osteogenesis in vertebrate tissue including administering chondrogenic or osteogenic precursor cells to the patient at a location proximate to the desired location of osteogenesis; further, administering BBP, and administering one of a TGF-β family member, such as BMP-2 or demineralized bone matrix.

In one embodiment, the invention may include a method of enhancing the rate or degree of calcification in vertebrate tissue including administering osteogenic cells to the patient at a location proximate to the desired location of calcification and further, administering BBP.

In one embodiment, the invention may include method of enhancing the rate or degree of osteogenesis in a vertebrate including treating vertebrate mesynchymal stem cells with one of a TGF-β family member, such as BMP-2 or demineralized bone matrix to induce osteogenesis of the cells. Further, treating the vertebrate mesynchymal stem cells with BBP; and administering the vertebrate mesynchymal stem cells to the patient at a location proximate to the desired location of osteogenesis.

For example, mammalian cells, such as mesenchymal stem cells can be harvested, from the patient or a cell donor. The cells may be injected in a location where bone formation or repair is desired (such as a fracture site or implant site), or first treated with BBP and/or BMP. The cells may then be re-administered to the patient, either systemically or at a selected site at which osteogenesis of calcification is desired. Additionally, the patient may by treated locally or systemically with at least one additional agent which effects osteogenesis or calcification.

Figure 12B:
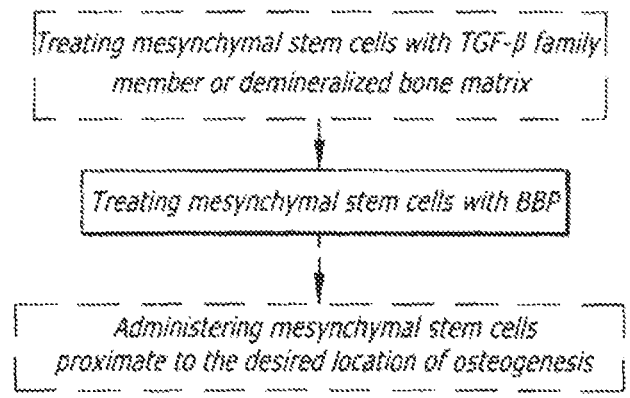
FIGS. 12 A & B depict flowcharts of exemplary methods of the invention.

FIGS. 12A and B depict flowcharts of exemplary methods of the invention, the steps of which may be performed in any order.

One embodiment of the invention may include an article of manufacture comprising BBP immobilized on a solid support. The solid support may further include a TGF-β family member, such as BMP-2 or demineralized bone matrix.

One embodiment of the invention may include an implant for use in vivo including, a substrate where at least the surface of the implant includes BBP. The implant may further include MSC, chondrocytic or osteoblastic progenitor cells. Further, the implant may be formed into the shape of a pin, screw, plate, or prosthetic joint, for example.

Figure 13A:
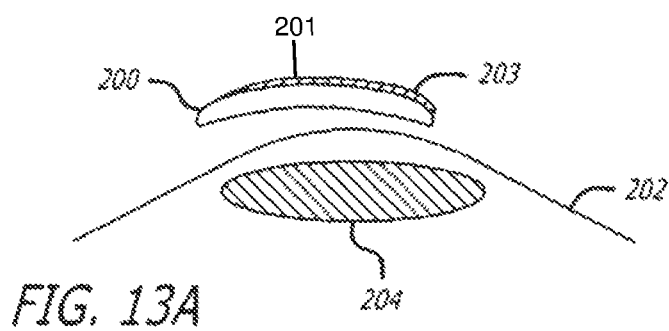
FIGS. 13 A & B are schematic depictions of two embodiments of the invention.

For example, FIGS. 13A & B depict two embodiments of the present invention. In FIG. 13A, the invention may include implants or grafts (200) for use in the body comprising, a substrate having a surface (201), wherein at least the surface of the implant includes BBP (203) in an amount sufficient to induce, calcification or osteogenesis in the surrounding tissue. The implant may include mesynchymal stem cell, chondrogenic or osteogenic cells expressing BBP, and/or BMP-2, demineralized bone matrix, or collagen cultures. The implant may be in the form of, but are not limited to pins, screws, plates or prosthetic joints which may be placed in the proximity of or in contact with a bone (202) that are used to immobilize a fracture, enhance bone formation, or stabilize a prosthetic implant by stimulating formation or repair of a site of bone removal, fracture or other bone injury (204).

Figure 13B:
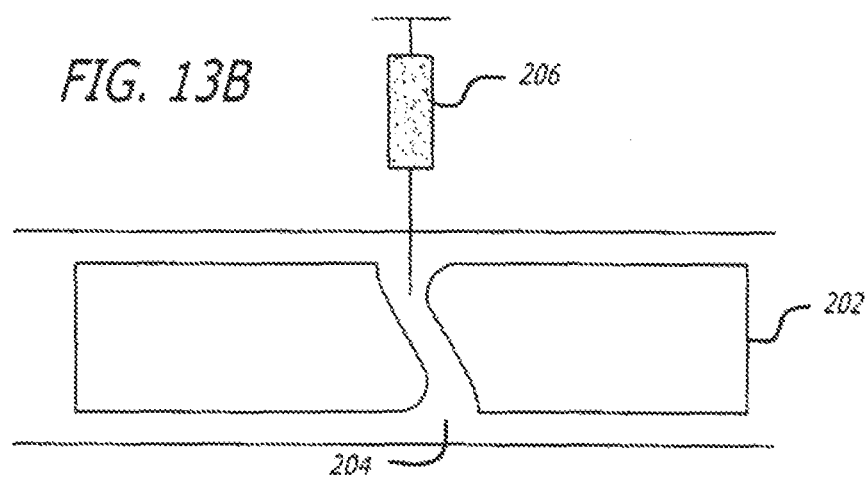

As shown in FIG. 13B, the invention may also include the in vitro (such as on cultures of collagen or chondrocytes) or in vivo application of at least BBP containing composition or BBP expressing cells (206) in the proximity of or in contact with a bone (202), an implant (200) at a site of bone removal, fracture or other bone injury (204) where osteogenesis and/or calcification is desired. The BBP composition may be applied in combination with other agents such as BMP-2, demineralized bone matrix, or collagen cultures.

For example, the use of stem cells for treating bone related disorders in humans has also been examined. Infusion of osteoblastic progenitor stem cells from a healthy individual into a diseased individual has been shown to improve bone density in these patients (OI). Cells may be pretreated with BMP and BPP, or applied concurrently therewith.

In one embodiment, the invention may include a monoclonal or polyclonal antibody having selective binding to any portion of BBP, or the BBP portion of the BBP precursor, SSP-24.

BBP or fragments thereof may be fused (for example by recombinant expression or in vitro covalent methods) to an immunogenic polypeptide and this, in turn, may be used to immunize an animal in order to raise antibodies against BBP. Antibodies are recoverable from the serum of immunized animals. Alternatively, monoclonal antibodies may be prepared from cells from the immunized animal in conventional fashion. Immobilized antibodies may be useful particularly in the detection or purification of BBP.

Two examples of specific peptide sequences against which rabbit polyclonal antibodies have been generated include: (1) An antibody against the peptide sequence "IQETTCRRESEADPATCDFQRGYHVPVAVCRST-VRMSAEQV" (FIG. 11—SEQ. ID NO: 3) that reacts with both bovine and human SSP-24, the BBP precursor. This antibody was generated in rabbits immunized with the synthetic peptide indicated above. Further, (2) An antibody directed against the sequence "CGEPLYEPSREMRRN" (FIG. 11—SEQ. ID NO: 4) that was also produced in rabbits immunized with a synthetic peptide corresponding to the indicated sequence. This second antibody reacts with bovine SSP-24. The N-terminal cysteine is not a part of the native SSP-24 sequence; but is preferably included to allow the peptide to be conjugated to chromatographic resins for affinity chromatography. Additional peptide sequences may be identified for specific binding to BBP, and sequences may be selected so as to create an antibody having selective binding with BBP, but so as to not interfere with BBP binding, such as the region of BBP which binds with BMP-2 or other TGF-β family members.

Antibodies against the sequences above, corresponding sequences in the mouse, human, and rat genome, or any derivatives of the immunogenic sequences are also useful in this invention. These antibodies are useful in at least to the extent that they recognize the BBP amino acid sequence with high specificity. Such antibodies may also be useful in inhibiting protein specific interactions of BBP with other molecules where the antibody binds to a location on the peptide which interacts with other molecules. The inhibition of BBP activity in situations where the rate or degree of chondogenesis or osteogenesis may be modified.

In one embodiment the invention, antibodies specific for BBP may be useful in decreasing the degree or rate of osteogenesis by BMP-2 in vertebrate cells or decreasing degree or rate of calcification in vertebrate cells, or more specifically in mammalian chondrogenic or osteoblastic precursor cells.

One embodiment of the invention may also include a method of using BBP selective antibodies to detect the presence of SSP-24/BBP in sample (including but not limited to a cell culture, tissue sample, peptide fraction, Western blot) including exposing the sample to the BBP selective antibody and visualizing the complex of SSP-24/BBP and BBP antibody.

In one embodiment of the invention, BBP antibodies may be used for the affinity purification of the BBP from recombinant cell culture or natural sources. BBP antibodies that do not detectably cross-react with other growth factors can be used to purify BBP from these other family members.

In one embodiment, the invention may include a nucleic acid construct comprising a DNA or RNA nucleic acid sequence encoding BBP, or modified sequences corresponding to the modified amino sequences described above.

The invention may also include, an expression vector operatively linked to a nucleic acid sequence encoding BBP, or precursor SSP-24 Further, a transformant may be obtained by introducing the nucleic acid construct encoding for BBP, or its precursor SSP-24 into a host cell.

Practice of this invention may include the use of an oligonucleotide construct comprising a sequence coding for BBP and for a promoter sequence operatively linked in a mammalian or a viral expression vector. Expression and cloning vectors contain a nucleotide sequence that enables the vector to replicate in one or more selected host cells. Generally, in cloning vectors this sequence is one that enables the vector to replicate independently of the host chromosomes, and includes origins of replication or autonomously replicating sequences. Such cloning vectors are well known to those of skill in the art. Expression vectors, unlike cloning vectors, may contain an inducible or constitutive promoter which is recognized by the host organism and is operably linked to the BBP nucleic acid. The nucleic acid may be operably linked when it is placed into a functional relationship with another nucleic acid sequence. For example, DNA for a pre-sequence or secretory leader is operably linked to DNA for a polypeptide if it is expressed as a pre-protein which participates in the secretion of the polypeptide.

One embodiment of the invention may also include a method of using DNA or RNA nucleic acid sequences complimentary and having specific binding for the DNA or RNA sequences encoding BBP to detect the presence of BBP DNA or RNA in a sample, respectively (including but not limited to a cell culture, tissue sample, nucleic acid fraction, or Southern or Northern blot) including exposing the sample to the complimentary BBP DNA or RNA sequences and visualizing the complex of hybrids.

Example 1: Extraction and Separation of Non-Collagenous Bone Proteins (NPCs)

Methods:

NCPs were extracted from defatted, demineralized human cortical bone powder with 4 M GuHCl, 0.5 M CaCl$_2$, 2 mM N-ethylmalemide, 0.1 mM benzamidine HCl, and 2 mM NaN$_3$ for 18 hr at 6° C. Residual collagen and citrate-soluble NCPs were extracted by dialysis against 250 mM citrate, pH 3.1 for 24 hours at 6° C. The residue was pelleted by centrifugation (10,000×g at 6° C. for 30 min), defatted with 1:1 (v/v) chloroform:methanol for 24 hr at 23° C., collected by filtration and dried at 22° C. The material was resuspended in 4 M GuHCl, dialyzed against 4 M GuHCl, 0.2% (v/v) Triton X-100, 100 mM Tris-HCl, pH 7.2 for 24 hr at 6° C., then dialyzed against water, and centrifuged at 10,000×g for 30 min at 6° C. The pellet was lyophilized and subsequently separated by hydroxyapatite chromatorgraphy.

Chromatography was conducted using a BioLogic chromatography workstation with a CHT-10 ceramic hydroxyapatite column (BioRad, Hercules, Calif.). Bovine BMP/NCP was solublized in 6 M urea, 10 mM sodium phosphate, pH 7.4. The sample was loaded onto the hydroxyapatite column and the unbound fraction was collected. Bound proteins were eluted with increasing concentration of sodium phosphate to 300 mM over a linear gradient of five column volumes. Five ml fractions were collected during the course of the run. The fraction which separated at 180 mM phosphate was separated further by SDS-PAGE electrophoresis. A band corresponding to a $M_r$ of 18.5 was excised and submitted for sequence analysis by matrix assisted laser-desorption ionization/time of flight mass spectroscopy (MALDI/TOF MS).

Results: Sequence Identification and Analysis:

The fraction of bBMP/NCP which eluted from hydroxyapatite at 180 mM phosphate was separated by SDS-PAGE electrophoresis and the material with a $M_r$ of 18.5 kD was submitted for MALDI/TOF MS analysis. The major protein component of this material was determined to be a fragment of SPP-24 on the basis of six peptides with sequences identical to regions of that protein. (Hu, et al., Isolation and molecular cloning of a novel bone phosphoprotein related in sequence to the cystatin family of thiol protease inhibitors. J. Biol. Chem. 270:431-436, 1995.) The sequences of these peptides are shown in Table 1.

TABLE 1

Identification of the 18.5 kD protein by MALDI/TOF mass spectroscopy and peptide fingerprinting.

| Expected Mass [a] | Observed Mass [a] | Peptide Sequence |
|---|---|---|
| 1526.574 | 1526.53 | ESEADPATCDFQR * |
| 1411.600 | 1411.71 | VNSQSLSPZLFR |
| 1291.406 | 1291.41 | SRGEPLZEPSR |
| 1249.409 | 1249.48 | NSZLLGLTPDR |
| 1158.363 | 1158.27 | GZHVPVAVCR * |

* modified cystein;
[a] = peptide masses are expressed as [M + H$^+$]

Analysis of this sequence with the SWISS-PROT data base revealed the cystatin-like domain which had been previously described, but no other sequence similarities of relevance to bone metabolism. (Hu, et al.) However, it is known from other work that other cystatin-like proteins interact with proteins having a role in bone metabolism. Specially, members of the cystatin family have TGF-β and BMP-2 binding properties based on similarities to the TGF-β receptor. (Brown, et al., Friends and relations of the cystatin superfamily—new members and their evolution: Protein Sci. 6:5-12, 1997; Demetriou, et al., Fetuin/α2-HS glycoprotein is a transforming growth factor-β type II receptor mimic and cytokine antagonist. J. Biol. Chem. 271: 12755-12761, 1996.) However, fetuin antagonizes BMP activity. (Hu, et al.) Therefore, a manual comparison was made of the cystatin-like region of SPP-24 and the cystatin-like domain of fetuin.

FIG. 1B is a partial amino acid sequence of the bovine SSP-24, the BMP-2 homology region, and the TGF-β receptor II homology domain. Underlined amino acids have been confirmed to be present by mass spectroscopy. (GenBank Accession Number U08018; Hu, et al.)

Two regions of interest were identified in the cystatin-like region of SPP-24. One region had some sequence similarity to BMP-2, whereas the other region had sequence similarity to the TGF-β receptor II homology domain of fetuin. That part of the sequence of SPP-24 which contains these two regions is shown in FIG. 1B.

Comparisons of the two regions of interest to human BMP-2 and human TGF-β receptor II are shown in FIGS. 2 and 3. FIG. 2 is an amino acid sequence alignment of human BMP-2 and the BMP-2 homology region in bovine SPP-24. FIG. 3 is an amino acid sequence alignment of bovine fetuin and human TGF-β receptor II (top) and of human TGF-β receptor II and the TGF-β receptor II homology domain of bovine SPP-24 (corresponding to BBP)(bottom). Alignment of the SPP-24, fetuin, human BMP-2, and human TGF-β receptor II sequences was accomplished using the T-Coffee program. (Notredame, et al, T-Coffee: A novel method for multiple sequence alignments. J. Molecular Biol. 302:205-217, 2000.) Synthetic peptides corresponding to these two regions were obtained and subjected to chemical and in vivo analysis as described below.

Example 2: In Vivo Activity of BBP

Methods:

The osteogenic activity of material was tested using male Swiss-Weber mice aged 8 to 10 weeks were used (Taconic Farms, Germantown, N.Y.). Prior to the assay, the BBP was solubized and lyophilized into 2 mg of atelocollagen. The dried material was placed in a #5 gelatin capsule and sterilized by exposure to chloroform vapor. To conduct the assay, mice were anesthetized using 1% isoflurane delivered in oxygen at 2 l/min through a small animal anesthesia machine (VetEquip, Pleasanton, Calif.). Animals were affixed to a surgery board and the fur over the hindquarters shaved. The skin was cleaned with 70% ethanol and a midline incision made over the spine adjacent to the hindquarters. Blunt dissection with scissors was used to expose the quadriceps muscle on one side. A small pouch was made in the muscle using the point of scissors and the #5 capsule containing the test material was inserted into the pouch. The skin was then closed with three 11 mm Michel surgical clips and the animal returned to its cage for monitoring.

After 21 days the animals were killed and the hindquarter removed. Radiological examination of the specimens was accomplished using a small parts X-Ray cabinet (Faxitron, Wheeling, Ill.). For quantization of bone formation, bone area and the bone mineral content (BMC) of an area of interest encompassing the site of ectopic bone formation was determined using a PIXImus2 small animal densitometer (GE Lunar, Madison, Wis.). Specimens were then placed in buffered formalin and submitted for routine processing for histological examination.

Various amounts of rhBMP-2 and BBP were combined and prepared for implantation. All possible combinations of the following amounts were used in pilot studies, rhBMP-2: 0 μg, 0.05 μg, 0.5 μg, 5 μg, and 50 μg; BBP: 0 μg, 50 μg, and μg 500 mg. Samples of 5 μg of rhBMP-2 were used in more extensive subsequent studies because that amount consistently produced an amount of ectopic bone that was neither too large nor too small for reliable analysis.

Results:

BBP was tested alone and in combination with rhBMP-2.

FIG. 4 is a radiogram of mouse hind quarters 21 days after implantation of 500 μg of BBP in atelocollagen (top) or atelocollagen alone (bottom). When implanted alone with carrier, BBP induced calcification.

Figure 5:
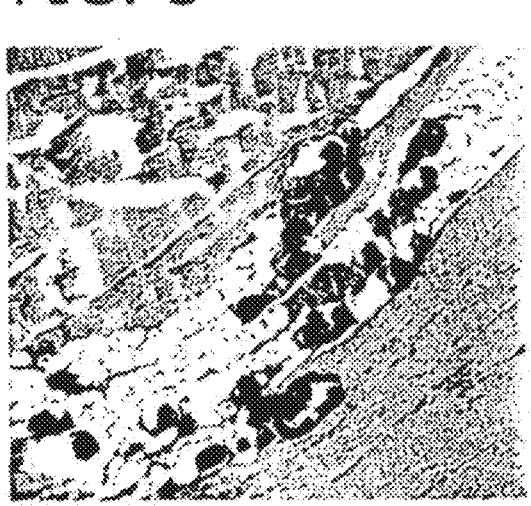
FIG. 5 is a histological section of mouse muscle 21 days after implantation of 500 µg of BBP in atelocollagen. (H & E stain. Original magnification 100×.)

FIG. 5 is a histological section of mouse muscle 21 days after implantation of 500 μg of BBP in atelocollagen. Note the dystrophic calcification primarily associated with intramuscular adipose tissue. (H & E stain. Original magnification 100×.)

When 500 μg of BBP with sequence similarity to the TGF-β receptor II was implanted with 5 μg of rhBMP-2 the amount of ectopic bone formed, as measured by densitometry, was consistently greater than the amount of bone formed in animals into which identical amounts of the rhBMP-2 alone were implanted.

Figure 6:
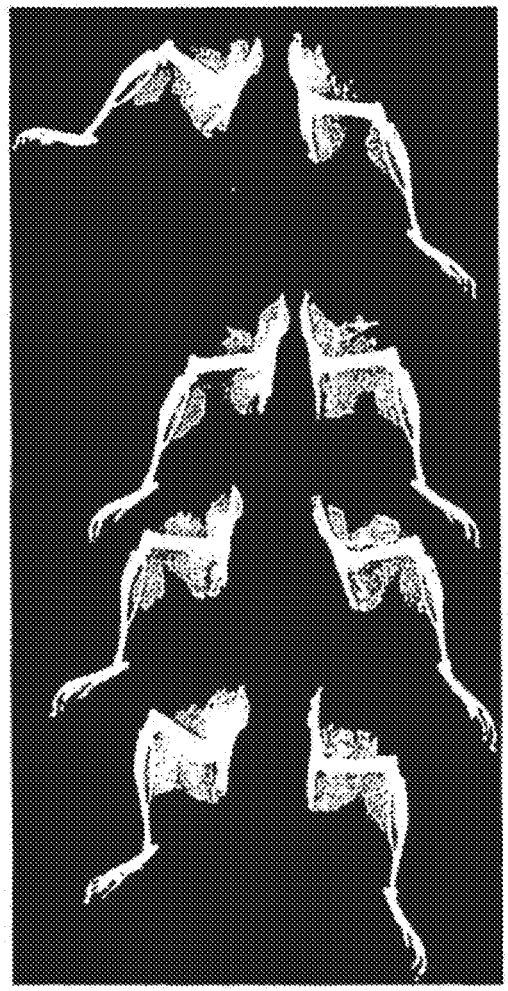
FIG. 6 are radiograms of mouse hind quarters 21 days after implantation of 5 µg of rhBMP-2 (left) or 5 µg of rhBMP-2 plus 500 mg of BBP (right).

FIG. 6 are radiograms of mouse hind quarters 21 days after implantation of 5 μg of rhBMP-2 (left) or 5 μg of rhBMP-2 plus 500 mg of BBP (right). Note the increased opacity associated with the samples containing both rhBMP-2 and BBP.

Furthermore, implants that contained both the peptide and rhBMP-2 produced detectable cartilage and bone earlier than implants of BMP-2 alone.

Figure 7:
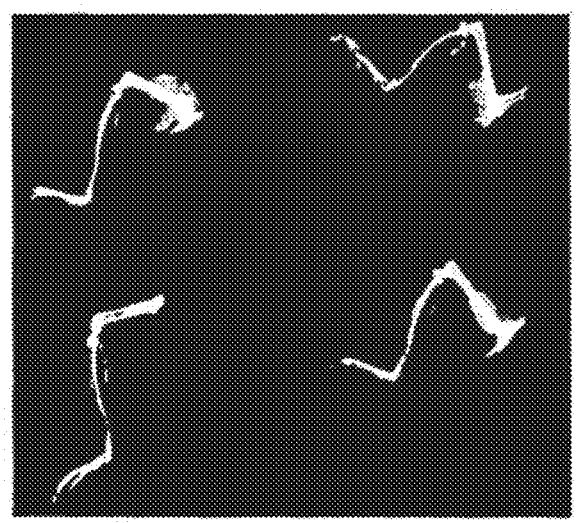
FIG. 7 are radiograms of mouse hind quarters 9 (top) and 12 (bottom) days after implantation of 5 µg of rhBMP-2 (left) or 5 µg of rhBMP-2 plus 500 mg of BBP (right).

FIG. 7 are radiograms of mouse hind quarters 9 (above) and 12 (below) days after implantation of 5 μg of rhBMP-2 (left) or 5 μg of rhBMP-2 plus 500 mg of BBP (right). Note the appearance of calcification in the sample from the day 9 sample containing both rhBMP-2 and BBP but not the sample containing BMP-2 alone.

Figure 8A:
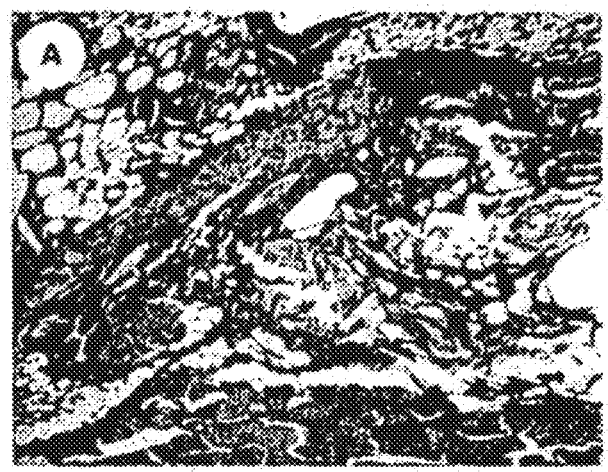
FIGS. 8 A & B are histological sections of mouse hind quarters 9 days after implantation of 5 µg of rhBMP-2 alone (A) or 5 µg of rhBMP-2 plus 500 µg of BBP (B).
Figure 8B:

FIG. 8 are histological sections of mouse hind quarters 9 days after implantation of 5 μg of rhBMP-2 alone (A) or 5 μg of rhBMP-2 plus 500 μg of BBP (B). Note the abundant cartilage in the BMP+BBP specimen whereas the BMP alone specimen shows the earlier stages of inflammation and mesodermal cell proliferation.

TABLE 2

Densitometric quantitation of ectopic bone formation with various amounts of BBP implanted with 5 μg of rhBMP-2. Mean, SE (n).

| BBP (μg) | 0 | 50 | 500 |
|---|---|---|---|
| Bone Area (cm²) | 0.089 ± 0.0336 (12)* | 0.159 ± 0.0606 (8) | 0.226 ± 0.0270 (12)* |
| Bone Mineral Content (g) | 0.00189 ± 0.00084 (12)** | 0.00388 ± 0.0017 (8) | 0.00528 ± 0.00068 (12)** |

*p = 0.0044;
**p = 0.0049

Example 3: Surface Plasmon Resonance to Determine the Interaction of BMP-2 and the Synthetic Peptide Methods:

The binding interaction between rhBMP-2 and BBP was characterized using surface plasmon resonance employing a Biacom X instrument (Biacore, Piscataway, N.J.). Buffers and chips for the procedure were obtained from Biacore. RhBMP-2 was dialyzed into 10 mM sodium acetate, pH 5.5 at a concentration of 1 mg/ml. This material was then attached to a CM-5 sensor chip using reagents and procedures supplied by the manufacturer. Running buffer was 10 mM HEPES, pH 7.4, 150 mM NaCl, 3 mM EDTA, 0.005% Surfactant P20. The peptide was dissolved in running buffer at concentrations ranging from $1 \times 10^{-5}$ to $1 \times 10^{-4}$ M. Flow rates from 5 to 50 μl/min and injection volumes of 20 to 100 μl were employed. The regeneration solution was 10 μM glycine-HCl, pH 2.0.

Figure 9:
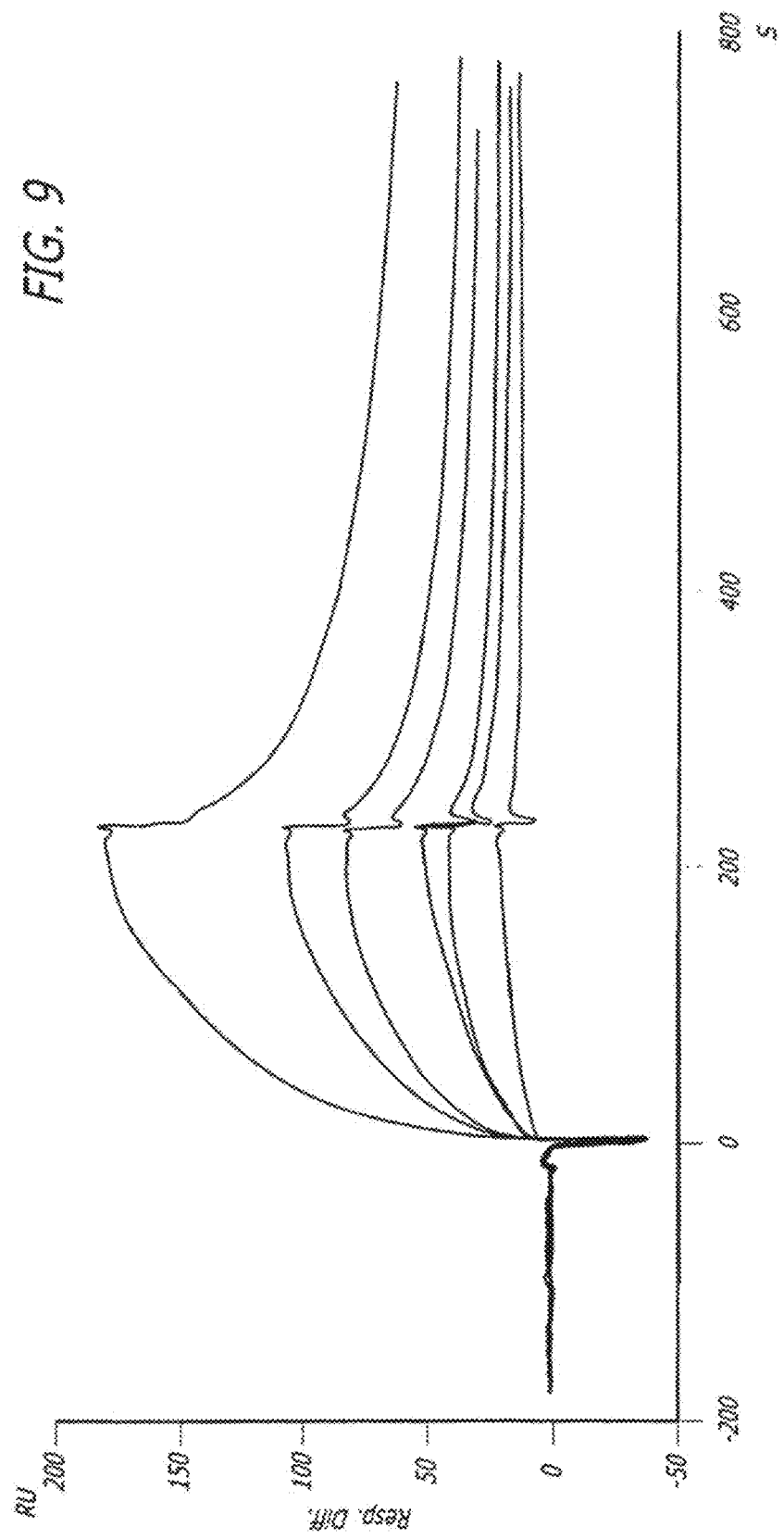
FIG. 9 is a surface plasmon resonance sensogram for the interaction of rhBMP-2 (affixed to the chip) and cyclized BBP at concentrations ranging from $1\times10^{-5}$ M $1\times10^{-4}$ M.

Results:

Results of the surface plasmon resonance studies to determine the interaction between rhBMP-2 and BBP are shown in FIG. 9.

FIG. 9 is a surface plasmon resonance sensogram for the interaction of rhBMP-2 (affixed to the chip) and cyclized BBP at concentrations ranging from $1 \times 10^{-5}$ M $1 \times 10^{-4}$ M. The estimated dissociation constant ($K_D$) for the interaction was $3 \times 10^{-5}$ M. When the BBP was decyclized by prior reduction with β-mercaptoethanol, no significant binding occurred.

Example 4: Residence Time Study: BBP and rhBMP-2

Methods:

Labeled rhBMP-2 was mixed with BBP or vehicle and applied to collagen sponges. The sponges were implanted into muscle pouches in rodents. At specified times (1, 3 and 7 days), the implants were removed and the amount of BMP remaining determined. Four animals were used in each group.

Results:

BBP increased retention of rhBMP-2 by a factor of about two. FIG. 10 is a bar graph depicting the percentage of rhBMP-2 retention over 1, 3 and 7 days in the presence or absence of BBP.

Discussion:

Increasing the retention of BMP at an implant site may improve the effectiveness of the BMP, and also reduce the amount required for the same therapeutic result.

While the specification describes particular embodiments of the present invention, those of ordinary skill can devise variations of the present invention without departing from the inventive concept.

Example 5: In Vivo Activity of Human BBP

Methods:

The methods of Example 5 were utilized to test the activity of hBBP in eight mice in the hindquarter ectopic bone formation assay method using 5 μg rhBMP-2 alone (control) or 5 μg rhBMP-2 plus 0.05 mg human BBP (hBBP). After 4 weeks, the animals were killed and the hindquarter removed. X-ray and DEXA analysis were conducted.

Results:

hBBP was tested in combination with rhBMP-2.

When implanted, hBBP with BMP resulted in a greater amount of calcification induction than BMP alone.

TABLE 3

Densitometric quantitation of ectopic bone formation with various amounts of BBP implanted with 5 μg of rhBMP-2. Mean, SE (n).

| Group | Mean BMC content (g) |
|---|---|
| rhBMP-2 (5 μg) | 0.00775 |
| hBBP (0.05 mg) + rhBMP-2 (5 μg) | 0.01125 |

The invention claimed is:

1. An article of manufacture comprising an implant, wherein said implant has a surface, and wherein said surface includes a peptide having the amino acid sequence of SEQ ID No. 13, or a fragment thereof, wherein said peptide or fragment increases the degree or rate of osteogenesis or calcification in vertebrates.

2. The article of manufacture of claim 1 wherein the implant further includes one or more of TGF-beta, BMP-2, BMP-4, BMP-7 or demineralized bone matrix.

3. The article of manufacture of claim 1 wherein the implant further includes mesenchymal stem cells.

4. The article of manufacture of claim 3 wherein the mesenchymal stem cells secrete one or more growth factors.

5. The article of manufacture of claim 4 wherein the growth factor is a TGF-beta family member.

6. The article of manufacture of claim 1 wherein the implant further includes chondrogenic or osteogenic precursor cells.

7. The article of manufacture of claim 6 wherein the chondrogenic or osteogenic precursor cells secrete one or more growth factors.

8. The article of manufacture of claim 7 wherein the growth factor is a TGF-beta family member.

9. The article of manufacture of claim 1 wherein said implant is formed into the shape of a pin, screw, plate, or prosthetic joint.

10. The article of manufacture of claim 1 wherein said peptide is immobilized on the surface of said implant.

11. An article of manufacture comprising a solid support, wherein said solid support includes a peptide having the amino acid sequence of SEQ ID No. 13, or a fragment thereof, wherein said peptide or fragment increases the degree or rate of osteogenesis or calcification in vertebrates.

12. The article of manufacture of claim 11 wherein said solid support has a surface, and wherein said peptide is immobilized on said surface.

13. The article of manufacture of claim 11 wherein the solid support further includes one or more of TGF-beta, BMP-2, BMP-4, BMP-7 or demineralized bone matrix.

14. The article of manufacture of claim 11 wherein the solid support further includes mesenchymal stem cells.

15. The article of manufacture of claim 14 wherein the mesenchymal stem cells secrete one or more growth factors.

16. The article of manufacture of claim 15 wherein the growth factor is a TGF-beta family member.

17. The article of manufacture of claim 11 wherein the solid support further includes chondrogenic or osteogenic precursor cells.

18. The article of manufacture of claim 17 wherein the chondrogenic or osteogenic precursor cells secrete one or more growth factors.

19. The article of manufacture of claim 18 wherein the growth factor is a TGF-beta family member.

20. A method of enhancing the degree or rate of osteogenesis or calcification in vertebrate tissue comprising applying to the tissue an implant, wherein said implant has a surface, and wherein said surface includes a peptide having the amino acid sequence of SEQ ID No. 13, or a fragment thereof, wherein said peptide or fragment increases the degree or rate of osteogenesis or calcification in vertebrates.

21. The method of claim 20 wherein implant is applied to the tissue at a location proximate to the desired location of osteogenesis or calcification.

22. The method of claim 20 wherein the implant further includes mesenchymal stem cells.

23. The method of claim 22 wherein the mesenchymal stem cells secrete one or more growth factors.

24. The method of claim 23 wherein the growth factor is a TGF-beta family member.

25. The method of claim 20 wherein the implant further includes chondrogenic or osteogenic precursor cells.

26. The method of claim 25 wherein the chondrogenic or osteogenic precursor cells secrete one or more growth factors.

27. The method of claim 26 wherein the growth factor is a TGF-beta family member.

* * * * *

SEQUENCE LISTING

<160> NUMBER OF SEQ ID NOS: 33

<210> SEQ ID NO 1
<211> LENGTH: 19
<212> TYPE: PRT
<213> ORGANISM: Bos sp.

```
<400> SEQUENCE: 1

Cys Arg Ser Thr Val Arg Met Ser Ala Glu Gln Val Gln Asn Val Trp
1               5                   10                  15

Val Arg Cys

<210> SEQ ID NO 2
<211> LENGTH: 57
<212> TYPE: DNA
<213> ORGANISM: Bos sp.
<220> FEATURE:
<221> NAME/KEY: CDS
<222> LOCATION: (1)..(57)

<400> SEQUENCE: 2 tgc aga agc acc gtg cgg atg tct gct gaa cag gtg cag aac gtg tgg      48
Cys Arg Ser Thr Val Arg Met Ser Ala Glu Gln Val Gln Asn Val Trp
1               5                   10                  15 gtt cgc tgc                                                           57
Val Arg Cys <210> SEQ ID NO 3
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ile Gln Glu Thr Thr Cys Arg Arg Glu Ser Glu Ala Asp Pro Ala Thr
1               5                   10                  15

Cys Asp Phe Gln Arg Gly Tyr His Val Pro Val Ala Val Cys Arg Ser
                20                  25                  30

Thr Val Arg Met Ser Ala Glu Gln Val
            35                  40

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Cys Gly Glu Pro Leu Tyr Glu Pro Ser Arg Glu Met Arg Arg Asn
1               5                   10                  15

<210> SEQ ID NO 5
<211> LENGTH: 200
<212> TYPE: PRT
<213> ORGANISM: Bos sp.

<400> SEQUENCE: 5

Met Ala Met Lys Met Leu Val Ile Phe Val Leu Gly Met Asn His Trp
1               5                   10                  15

Thr Cys Thr Gly Phe Pro Val Tyr Asp Tyr Asp Pro Ala Ser Leu Lys
                20                  25                  30

Glu Ala Leu Ser Ala Ser Val Ala Lys Val Asn Ser Gln Ser Leu Ser
            35                  40                  45

Pro Tyr Leu Phe Arg Ala Phe Arg Ser Ser Val Lys Arg Val Asn Ala
        50                  55                  60
```

-continued

Leu Asp Glu Asp Ser Leu Thr Met Asp Leu Glu Phe Arg Ile Gln Glu
 65                  70                  75                  80

Thr Thr Cys Arg Arg Glu Ser Glu Ala Asp Pro Ala Thr Cys Asp Phe
             85                  90                  95

Gln Arg Gly Tyr His Val Pro Val Ala Val Cys Arg Ser Thr Val Arg
                100                 105                 110

Met Ser Ala Glu Gln Val Gln Asn Val Trp Val Arg Cys His Trp Ser
            115                 120                 125

Ser Ser Ser Gly Ser Ser Ser Glu Glu Met Phe Phe Gly Asp Ile
        130                 135                 140

Leu Gly Ser Ser Thr Ser Arg Asn Ser Tyr Leu Leu Gly Leu Thr Pro
145                 150                 155                 160

Asp Arg Ser Arg Gly Glu Pro Leu Tyr Glu Pro Ser Arg Glu Met Arg
                165                 170                 175

Arg Asn Phe Pro Leu Gly Asn Arg Arg Tyr Ser Asn Pro Trp Pro Arg
            180                 185                 190

Ala Arg Val Asn Pro Gly Phe Glu
        195                 200

<210> SEQ ID NO 6
<211> LENGTH: 25
<212> TYPE: PRT
<213> ORGANISM: Homo sapiens

<400> SEQUENCE: 6

Phe Pro Leu Ala Asp His Leu Asn Ser Thr Asn His Ala Ile Val Gln
 1               5                  10                  15

Thr Leu Val Asn Ser Val Asn Ser Lys
            20                  25

<210> SEQ ID NO 7
<211> LENGTH: 25
<212> TYPE: PRT
<213> ORGANISM: Homo sapiens

<400> SEQUENCE: 7

Phe Pro Val Tyr Asp Tyr Asp Pro Ala Ser Leu Lys Glu Ala Leu Ser
 1               5                  10                  15

Ala Ser Val Ala Lys Val Asn Ser Gln
            20                  25

<210> SEQ ID NO 8
<211> LENGTH: 19
<212> TYPE: PRT
<213> ORGANISM: Bos sp.

<400> SEQUENCE: 8

Cys Asp Ile His Val Leu Lys Gln Asp Gly Gln Phe Ser Val Leu Phe
 1               5                  10                  15

Thr Lys Cys

<210> SEQ ID NO 9
<211> LENGTH: 18
<212> TYPE: PRT
<213> ORGANISM: Homo sapiens

-continued

```
<400> SEQUENCE: 9

Cys Val Ala Val Trp Arg Lys Asn Asp Glu Asn Ile Thr Leu Glu Thr
1               5                   10                  15

Val Cys

<210> SEQ ID NO 10
<211> LENGTH: 19
<212> TYPE: PRT
<213> ORGANISM: Bos sp.

<400> SEQUENCE: 10

Cys Arg Ser Thr Val Arg Met Ser Ala Glu Gln Val Gln Asn Val Trp
1               5                   10                  15

Val Arg Cys

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (6)..(6)
<223> OTHER INFORMATION: Semi-conservative amino acid
<220> FEATURE:
<221> NAME/KEY: MOD_RES
<222> LOCATION: (7)..(7)
<223> OTHER INFORMATION: Conservative amino acid
<220> FEATURE:
<221> NAME/KEY: MOD_RES
<222> LOCATION: (9)..(11)
<223> OTHER INFORMATION: Semi-conservative amino acid
<220> FEATURE:
<221> NAME/KEY: MOD_RES
<222> LOCATION: (13)..(14)
<223> OTHER INFORMATION: Semi-conservative amino acid
<220> FEATURE:
<221> NAME/KEY: MOD_RES
<222> LOCATION: (16)..(16)
<223> OTHER INFORMATION: Semi-conservative amino acid
<220> FEATURE:
<221> NAME/KEY: MOD_RES
<222> LOCATION: (17)..(18)
<223> OTHER INFORMATION: Conservative amino acid

<400> SEQUENCE: 11

Cys Arg Ser Thr Val Xaa Xaa Ser Xaa Xaa Xaa Val Xaa Xaa Val Xaa
1               5                   10                  15

Xaa Xaa Cys

<210> SEQ ID NO 12
<211> LENGTH: 57
<212> TYPE: DNA
<213> ORGANISM: Artificial Sequence
<220> FEATURE:
<223> OTHER INFORMATION: Description of Artificial Sequence: Synthetic
      consensus polynucleotide
<220> FEATURE:
<221> NAME/KEY: modified_base
<222> LOCATION: (16)..(18)
<223> OTHER INFORMATION: a, c, g, t, unknown or other
<220> FEATURE:
<221> NAME/KEY: modified_base
<222> LOCATION: (25)..(33)
<223> OTHER INFORMATION: a, c, g, t, unknown or other
```

```
<220> FEATURE:
<221> NAME/KEY: modified_base
<222> LOCATION: (37)..(42)
<223> OTHER INFORMATION: a, c, g, t, unknown or other
<220> FEATURE:
<221> NAME/KEY: modified_base
<222> LOCATION: (46)..(48)
<223> OTHER INFORMATION: a, c, g, t, unknown or other

<400> SEQUENCE: 12
tgcagaagca ccgtgnnnyy ytctnnnnnn nnngtgnnnn nngtgnnntt tttttgc      57

<210> SEQ ID NO 13
<211> LENGTH: 19
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Ala or Val

<400> SEQUENCE: 13

Cys Arg Ser Thr Val Lys Val Ser Xaa Gln Gln Val Gln Gly Val His
 1               5                  10                  15

Ala Arg Cys

<210> SEQ ID NO 14
<211> LENGTH: 57
<212> TYPE: DNA
<213> ORGANISM: Homo sapiens

<400> SEQUENCE: 14
tgcagaagca ccgtgaaggt atctgcccag caggtgcagg gcgtgcatgc tcgctgc      57

<210> SEQ ID NO 15
<211> LENGTH: 19
<212> TYPE: PRT
<213> ORGANISM: Sus sp.

<400> SEQUENCE: 15

Cys Arg Ser Thr Val Gln Ile Ser Ala Glu Lys Val Gln Asp Val Trp
 1               5                  10                  15

Val Arg Cys

<210> SEQ ID NO 16
<211> LENGTH: 57
<212> TYPE: DNA
<213> ORGANISM: Sus sp.

<400> SEQUENCE: 16
tgcagaagca ccgtgcagat atctgctgag aaggtgcagg atgtgtgggt gcgttgt      57

<210> SEQ ID NO 17
<211> LENGTH: 19
<212> TYPE: PRT
<213> ORGANISM: Ovis sp.

<400> SEQUENCE: 17

Cys Arg Ser Thr Val Arg Met Ser Ala Glu Arg Val Gln Asp Val Trp
 1               5                  10                  15

Val Arg Cys
```

```
<210> SEQ ID NO 18
<211> LENGTH: 57
<212> TYPE: DNA
<213> ORGANISM: Ovis sp.

<400> SEQUENCE: 18
tgcagaagca ccgtgcggat gtctgctgaa cgcgtgcagg acgtgtgggt tcgctgc      57

<210> SEQ ID NO 19
<211> LENGTH: 19
<212> TYPE: PRT
<213> ORGANISM: Rattus sp.

<400> SEQUENCE: 19

Cys Arg Ser Thr Val Gln Met Ser Lys Gly Gln Val Lys Asp Val Trp
  1               5                  10                  15

Ala His Cys

<210> SEQ ID NO 20
<211> LENGTH: 57
<212> TYPE: DNA
<213> ORGANISM: Rattus sp.

<400> SEQUENCE: 20
tgcaggagca cagtgcagat gtccaaggga caggtgaagg atgtgtgggc tcactgc      57

<210> SEQ ID NO 21
<211> LENGTH: 19
<212> TYPE: PRT
<213> ORGANISM: Mus sp.

<400> SEQUENCE: 21

Cys Arg Ser Thr Val Gln Met Ser Lys Gly Gln Val Lys Asp Val Trp
  1               5                  10                  15

Ala His Cys

<210> SEQ ID NO 22
<211> LENGTH: 57
<212> TYPE: DNA
<213> ORGANISM: Mus sp.

<400> SEQUENCE: 22
tgcaggagca ctgtgcagat gtccaaggga caggtaaagg atgtgtgggc tcactgc      57

<210> SEQ ID NO 23
<211> LENGTH: 19
<212> TYPE: PRT
<213> ORGANISM: Gallus sp.

<400> SEQUENCE: 23

Cys Lys Ser Val Val Glu Val Ser Ser Glu Gln Ile Val Asn Val Ile
  1               5                  10                  15

Val Arg Cys

<210> SEQ ID NO 24
<211> LENGTH: 57
<212> TYPE: DNA
<213> ORGANISM: Gallus sp.

<400> SEQUENCE: 24
tgcaaaagcg ttgtagaagt ctccagtgag cagattgtga atgttattgt gcgatgc      57
```

<210> SEQ ID NO 25
<211> LENGTH: 19
<212> TYPE: PRT
<213> ORGANISM: Salmo sp.

<400> SEQUENCE: 25

Cys Thr Ala Arg Val Arg Val Thr Ala Glu Phe Thr Gln Val Val Ser
 1               5                  10                  15

Leu Asn Cys

<210> SEQ ID NO 26
<211> LENGTH: 57
<212> TYPE: DNA
<213> ORGANISM: Salmo sp.

<400> SEQUENCE: 26
tgcaccgcac gtgttcgcgt cactgcagag ttcactcagg ttgtgtccct gaactgt         57

<210> SEQ ID NO 27
<211> LENGTH: 19
<212> TYPE: PRT
<213> ORGANISM: Salmo sp.

<400> SEQUENCE: 27

Cys Thr Ala Arg Val Arg Val Thr Ala Glu Leu Thr Gln Val Val Ser
 1               5                  10                  15

Leu Asn Cys

<210> SEQ ID NO 28
<211> LENGTH: 57
<212> TYPE: DNA
<213> ORGANISM: Salmo sp.

<400> SEQUENCE: 28
tgcaccgcac gtgttcgtgt cactgcagag ctcactcagg ttgtgtccct gaactgt         57

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Ser Glu Ala Asp Pro Ala Thr Cys Asp Phe Gln Arg
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Asn Ser Gln Ser Leu Ser Pro Tyr Leu Phe Arg
 1               5                  10

<210> SEQ ID NO 31
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 31

Ser Arg Gly Glu Pro Leu Tyr Glu Pro Ser Arg
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Ser Tyr Leu Leu Gly Leu Thr Pro Asp Arg
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Tyr His Val Pro Val Ala Val Cys Arg
1               5                   10
```